United States Patent [19]

Katz et al.

[11] Patent Number: 4,853,413

[45] Date of Patent: * Aug. 1, 1989

[54] REPELLING ANIMALS WITH COMPOSITIONS COMPRISING CITRONELLYL NITRILE, CITRONELLOL AND, OPTIONALLY METHYL TERPENYL ETHER, LEMON OIL, CARYOPHYLLENE, ISOPULEGOL, ISOPULEGYL ACETATE AND QUININE OR ONE OR MORE OF ITS SALTS

[75] Inventors: Ira Katz, West Long Branch; Donald A. Withycombe, Lincroft, both of N.J.

[73] Assignee: International Flavors & Fragrances Inc., New York, N.Y.

[ * ] Notice: The portion of the term of this patent subsequent to Apr. 5, 2005 has been disclaimed.

[21] Appl. No.: 33,788

[22] Filed: Apr. 3, 1987

[51] Int. Cl.$^4$ .............. A01N 31/275; A01N 31/075; A01N 31/045

[52] U.S. Cl. .................... 514/526; 514/715; 514/724; 514/739; 514/918; 514/920

[58] Field of Search .............. 514/526, 715, 724, 739, 514/918, 920

[56] References Cited

U.S. PATENT DOCUMENTS

| | | | |
|---|---|---|---|
| 2,254,665 | 9/1941 | Ralston et al. | 514/724 |
| 2,578,595 | 12/1951 | Ralston et al. | 514/526 |
| 4,735,803 | 4/1988 | Katz et al. | 514/715 |

*Primary Examiner*—Douglas W. Robinson
*Assistant Examiner*—Roger Gobrogge
*Attorney, Agent, or Firm*—Arthur L. Liberman

[57] ABSTRACT

Described are animal control compositions and methods; which compositions comprise citronellyl nitrile, citronellol and, optionally, methyl terpenyl ether, lemon oil, caryophyllene, isopulegol, isopulegyl acetate and quinine or one or more of its salts. The compositions can be used "as is" or in the form of a "controlled release" composition whereby the citronellyl nitrile, citronellol and, optionally, methyl terpenyl ether, lemon oil, caryophyllene, isopulegol, isopulegyl acetate and quinine or one or more of its salts are intimately admixed (alone or with adjuvants including but not limited to other volatile, odorous ingredients) with a polymeric substance such as polyethylene in the form of pellets or functional articles, e.g., garbage bags.

6 Claims, 5 Drawing Sheets

GLC PROFILE FOR EXAMPLE I.
CRUDE

GLC PROFILE FOR EXAMPLE I

GLC PROFILE FOR EXAMPLE I.

REPELLING ANIMALS WITH COMPOSITIONS COMPRISING CITRONELLYL NITRILE, CITRONELLOL AND, OPTIONALLY METHYL TERPENYL ETHER, LEMON OIL, CARYOPHYLLENE, ISOPULEGOL, ISOPULEGYL ACETATE AND QUININE OR ONE OR MORE OF ITS SALTS

BACKGROUND OF THE INVENTION

This application relates to animal control compositions and methods, and more particularly relates to dog repellent compositions and to methods for repelling dogs.

It is frequently desired to exclude animals from certain areas. Such a need to limit the movements of animals ranges from controlling large and/or dangerous carnivores such as bears, wolves, coyotes and the like to controlling smaller animals such as rats, mice, squirrels and the like.

While the more desirable animals, including most of those mentioned above, can be controlled by such direct methods as baiting and trapping, it is usually undesirable to deal with domestic animals so severely. This is particularly true of domesticated animals such as dogs which are pets and are generally allowed access to many areas in and around human habitation. It would be desirable to provide ways for excluding such domesticated animals from specific areas without otherwise materially limiting their freedom of movement.

In the past attempts have been made to control domestic animals through the use of materials which would be repellent to the particular animal and a number of animal repellent materials are known, for example, aliphatic or alicyclic ketones containing from about 6 up to about 20 carbon atoms in a suitable carrier as disclosed and claimed in U.S. Pat. No. 3,474,176 issued Oct. 21, 1969. However, these prior art materials suffer from a number of deficiencies. Some of the materials are relatively ineffective and some of the more effective materials have unpleasant odors, in some cases such that they tend to be distasteful to humans, also. Other materials are so toxic that it is not possible to use them because of the possibility of accidental ingestion, either by the animals themselves or by humans.

Dog and cat repellent packaging materials are disclosed in Japanese published Patent Application (Kokai Tokkyo Koho No. 82/74,158 whereby polyolefin-paper packaging laminates were treated on the paper side with lemongrass oil for dog and cat repelling properties. For example, a polyethylene-kraft paper laminate was treated with a lemongrass oil emulsion and used for packaging food. This published Japanese Application is abstracted at Chem. Abstracts Vol. 97, No. 145944y.

German Offen. No. 1,248,361 published on Aug. 24, 1967 discloses an animal repellent consisting of formic acid, formaldehyde, butyric acid and ammonium sulfide and water. German Offen. No. 1,248,361 is abstracted at Chem. Abstracts Vol. 67, 1967 at 107669k.

Coyotes and dogs are indicated to be repelled by β-chloroacetyle chloride or cinnamaldehyde according to Lohner, et al, J. Wildl. Manage. 1976, 40(1) pages 145–150, abstracted at Chem. Abstracts, Vol. 84, No. 175119g.

Japan Kokai No. 76/19,129 discloses the use of ethylthiometon or isothioate as a repellent for dogs, cats and birds. The Japan Kokai No. 76/19,129 is abstracted at Chem. Abstracts 85:15377g.

German Offen. No. 2,525,686 published on Dec. 30, 1976 discloses a dog-repelling disinfectant composition containing pyridine, paraformaldehyde and formaldehyde. German Offen. No. 2,525,686 is abstracted at Chem. Abstracts, Vol. 86, No. 84765q.

Japan Kokai Tokkyo Koho No. 81/65,803 discloses the use of methyl nonyl ketone and/or methyl phenyl ketone and one or more of leaf aldehyde, leaf alcohol, cinnamic aldehyde and cinnamic alcohol as a repellent for dogs, cats and birds. Japan Kokai Tokkyo Koho No. 81/65,803 is abstracted at Chem. Abstracts 95:75495k.

French Pat. No. 2,495,469 published on June 11, 1982 discloses a dog repellent containing 1.5% Capsicum annum ext. (Mombassa EW 810280 containing capsaicin as the active ingredient) and 98.5% hexanol. French Pat. No. 2,495,469 is abstracted at Chem. Abstracts Vol. 97 No. 118286c.

French Pat. No. 2,527,902 published on Dec. 9, 1983 discloses the use of fennel seed and ethanol taken together with copper sulfate and ammonia as a dog repellent. French Pat. No. 2,527,902 is abstracted at Chem. Abstracts, Vol. 100, No. 134333c.

French Pat. No. 2,542,002 discloses adding terpenes (optionally halogenated), terpene alcohols and/or terpene esters to plastics, especially polyethylene garbage bags, thereby causing them to be free of unpleasant smells even when filled with malodorous materials, and to be avoided by animals. French Pat. No. 2,542,002 indicates that garbage bags prepared from this film and filled with kitchen wastes were not attacked by dogs, cats or rats, while those prepared without the terpenes were so attacked. French Pat. No. 2,542,002 is abstracted at Chem. Abstracts, Vol. 102, No. 7726z.

French Pat. No. 2,538,222 published on June 29, 1984 discloses a dog repellent comprising fennel oil, copper sulfate, ammonia and water. French Patent No. 2,538,222 is abstracted at Chem. Abstracts, Vol. 102, No. 41601q.

French Pat. No. 2,546,718 published on Dec. 7, 1984 discloses a cat and dog repellent composition containing fennel oil, marjoram oil, rosemary oil, copper sulfate, ammonia and water. French Pat. No. 2,546,718 is abstracted at Chem. Abstracts, Vol. 102, No. 199618k.

Nothing in the prior art, however, discloses the unobvious unexpected and advantageous animal repellent properties of the composition of matter of our invention containing citronellyl nitrile, citronellol and, optionally, methyl terpenyl ether, lemon oil, caryophyllene, isopulegol, isopulegyl acetate and quinine or one or more of its salts.

Olefinic nitriles are disclosed in the prior art as having organoleptic properties whereby they augment or enhance the aroma of perfume compositions or perfumed articles, for example:
 (i) U.S. Pat. No. 3,168,550 discloses the use of alpha geranyl propionnitrile, geranyl isobutyronitrile and 5,9-dimethyl-4,8-decadienyl nitrile for their organoleptic utilities in perfumery;
 (ii) U.S. Pat. No. 3,531,510 issued on Sept. 29, 1970 discloses "cis" and "trans" 5,7,7-trimethyl-3-octene nitrile and "cis" and "trans" 5,7,7-trimethyl-2-octene nitrile for their organoleptic properties in perfumery;
 (iii) U.S. Pat. No. 3,655,722 issued on Apr. 11, 1972 discloses the use of "cis" and "trans" 3,7-dimethyl-2,6-octadienenitrile, "cis" and "trans" 3,7-dimethyl-3,6-octadienenitrile and 7-methyl-3-methylene-6-octenenitrile for their organoleptic properties in perfumery; as does (iv) U.S. Pat. No. 3,553,110 issued on Jan. 5, 1971.

U.S. Pat. No. 4,173,543 issued on Nov. 6, 1979 (assigned to the assignee of the instant application International Flavors & Fragrances Inc.) and U.S. Pat. No. 4,255,460 issued on Mar. 10, 1981 (assigned to the assignee of the instant application, International Flavors & Fragrances Inc.) each disclose the use of the compound alpha-terpinyl methyl ether having the structure:

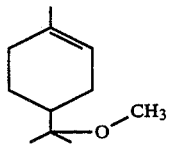

for its organoleptic properties.

These patents also disclose, for use as food flavorants, the combination of the alpha-terpinyl methyl ether with one or more of hundreds of compound including, inter alia, lemon essential oil (see line 53, column 13 of 4,255,460 and line 12 column 15 of U.S. Pat. No. 4,173,543). Nothing in either of U.S. Pat. Nos. 4,255,460 or 4,173,543 infers or expressly discloses the use of lemon essential oil taken together with the compound having the structure:

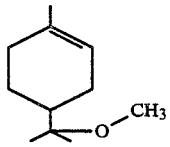

in repelling dogs or other mammalian species.

THE INVENTION

Figure 1:
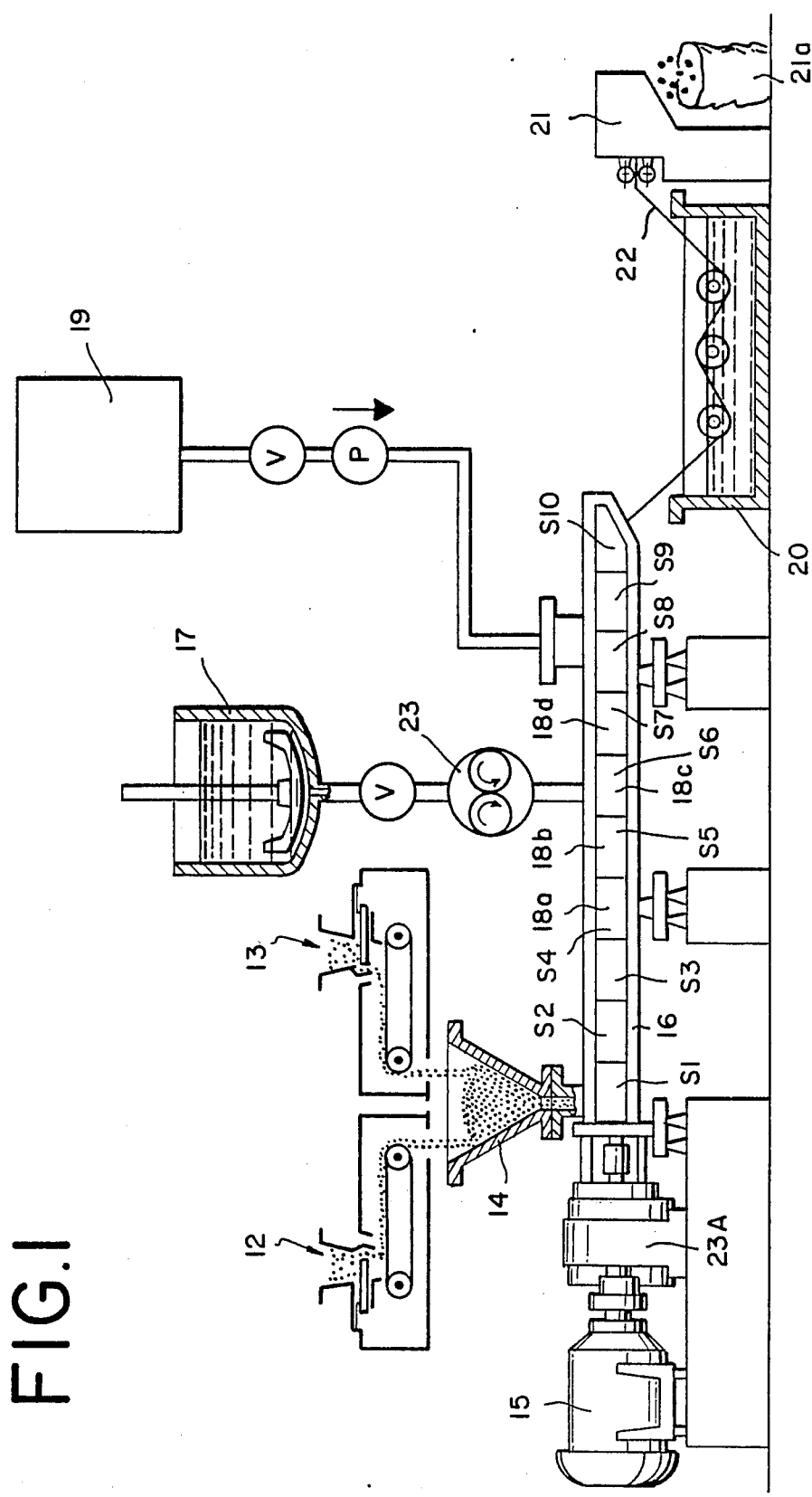
FIG. 1 is a cutaway side elevation schematic diagram of a screw extruder during the compounding of a resin with the fluidized animal repellent composition of matter of our invention containing citronellyl nitrile, citronellol and, optionally, methyl terpenyl ether, lemon oil, caryophyllene, isopulegol, isopulegyl acetate and quinine or one or more of its salts and incorporates pelletizing apparatus used in pelletizing the extruded composition of matter so produced as a result of the extrusion operation.

The invention comprises the novel compositions and component mixtures comprised in such compositions as well as the novel methods and steps of methods, specific embodiments of which are described hereinafter by way of example only and in accordance with what is now considered the preferred manner of practicing this invention.

Briefly, the compositions of this invention comprise a suitable carrier and:

(a) from about 40 parts by weight up to about 90 parts by weight of citronellyl nitrile which is a mixture containing from about 60 up to about 100% by weight of the compound having the structure:

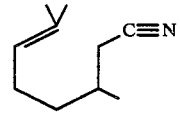

and from about 0 up to about 40% by weight of the compound having the structure:

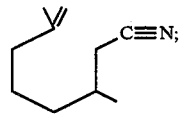

(b) from about 4 parts by weight up to about 20 parts by weight of citronellol which is a mixture of compounds containing from about 60% up to about 100% by weight of the compound having the structure:

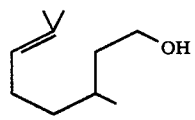

and from about 0 up to about 40% by weight of the compound having the structure:

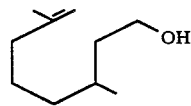

(c) from about 0 up to about 2 parts by weight of beta caryophyllene having the structure:

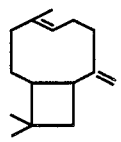

(d) from about 0 up to about 0.5 parts by weight of isopulegyl acetate having the structure:

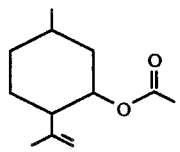

(e) from about 0 up to about 1.5 parts by weight of isopulegol having the structure:

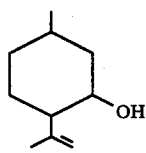

(f) from about 0 parts by weight up to about 50 parts by weight of alpha terpenyl methyl ether having the structure:

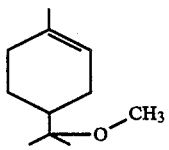

(g) from about 0 parts by weight up to about 50 parts by weight of lemon essential oil as hereinafter defined:

(h) from about 0 parts by weight up to about 25 parts by weight of quinine having the structure:

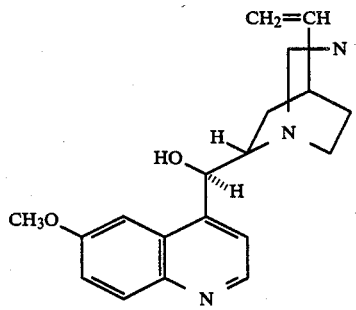

or one or more of its salts;

(i) optionally, other adjuvants including but not limited to volatile odorous ingredients.

If quinine or one or more of its salts are used in a composition of matter of our invention it is preferred that the quinine or one or more of its salts be in solution.

Preferably, the ranges of the ingredients of the composition of matter of our invention are as follows:

82–90% citronellyl nitrile;
9–17% citronellol;
0–2% beta caryophyllene;
0.0–0.5% isopulegyl acetate; and
0–1.2% isopulegol.

The foregoing composition is hereinafter collectively referred to as the "citronellyl nitrile/citronellol-containing composition of our invention".

The citronellyl nitrile/citronellol-containing compositions of our invention are present in the overall composition in amounts effective to repell animals, preferably dogs, from the area in which the compositions are applied. The method of this invention comprises treating an article or an area with the citronellyl nitrile/citronellol-containing compositions of our invention to repell animals from the treated ones. Unless otherwise indicated, all parts, proportions, percentages and ratios herein are by weight.

Some compositions of this invention have been found to be especially adapted for use in pressurized aerosol dispensing containers. Accordingly, in certain embodiments of this invention, the composition comprises citronellyl nitrile/citronellol-containing compositions of our invention, a propellent and generally a vehicle for the citronellyl nitrile/citronellol-containing compositions of our invention. Such compositions are very conveniently and economically dispensed from aerosol containers and rapidly produce the desired repellent action in the area sprayed.

Furthermore, the citronellyl nitrile/citronellol-containing compositions of our invention can be incorporated into a polymer such as polyethylene by standard techniques such as that disclosed in U.S. Pat. No. 4,521,541 issued on June 4, 1985, the disclosure for which is incorporated by reference herein; or by means of the technique set forth in U.S. Pat. No. 3,505,432 which discloses a method of incorporating a volatile material into a polyolefin which comprises:

(a) mixing a first amount of liquid polyolefin, e.g., polyethylene or polypropylene with a relatively large amount of volatile material to form a flowable mass;

(b) forming drops from said mass and causing substantially instantaneous solidification of said drops into polyolefin pellets having a relatively large amount of volatile material (e.g., the citronellyl nitrile/citronellol-containing composition of our invention) imprisoned therein;

(c) melting said pellets with a second amount of said polyolefin, said second amount being larger than said first amount; and (d) solidifying the melt of "(c)".

The articles disclosed in U.S. Pat. No. 4,247,498 issued on Jan. 27, 1981 are useful in conjunction with our invention. U.S. Pat. No. 4,247,498 discloses microporous polymers which are capable of containing volatile substances which we have discovered can be the citronellyl nitrile/citronellol-containing compositions of our invention in forms ranging from films to blocks in intricate shapes, from synthetic thermoplastic polymers such as olefinic condensation or oxidation polymers. In one embodiment of U.S. Pat. No. 4,247,498 the microporous polymers are characterized by relatively homogeneous three dimensional cellular structures having cells connected by pores of smaller dimensions. Also disclosed in U.S. Pat. No. 4,247,498 is a process for making microporous polymers from such thermoplastic polymers by heating a mixture of polymer and a compatible liquid (e.g., a volatile substance which could include the citronellyl nitrile/citronellol-containing compositions of our invention) to form a homogeneous solution, cooling said solution under non-equilibrium thermodynamic conditions to initiate liquid-liquid phase separation, and continuing said cooling until the mixture achieves a substantial handling strength. Also disclosed in said U.S. Pat. 4,247,498 are microporous polymer products which contain relatively large amounts of such functionally useful fluids as animal repellent compositions, e.g., the citronellyl nitrile/citronellol-containing compositions of our invention of our invention, and behave as solids.

The effective repellent substances are mixtures of:

(a) from about 40 parts by weight up to about 90 parts by weight of citronellyl nitrile which is a mixture containing from about 60 up to about 100% by weight of the compound having the structure:

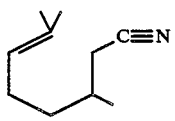

and from about 0 up to about 40% by weight of the compound having the structure:

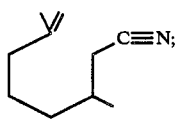

(b) from about 4 parts by weight up to about 20 parts by weight of citronellol which is a mixture of compounds containing from about 60% up to about 100% by weight of the compound having the structure:

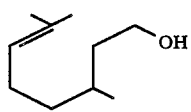

and from about 0 to about 40% by weight of the compound having the structure:

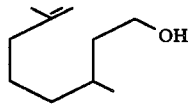

(c) from about 0 up to about 2 parts by weight of beta caryophyllene having the structure:

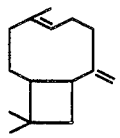

(d) from about 0 up to about 0.5 parts by weight of isopulegyl acetate having the structure:

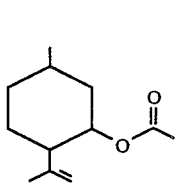

(e) from about 0 up to about 1.5 parts by weight of isopulegol having the structure:

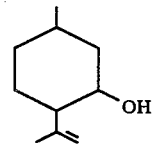

(f) from about 0 parts by weight up to about 50 parts by weight of alpha terpenyl methyl ether having the structure:

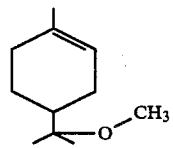

(g) from about 0 parts by weight up to about 50 parts by weight of lemon essential oil as hereinafter defined:

(h) from about 0 parts by weight up to about 25 parts by weight of quinine having the structure:

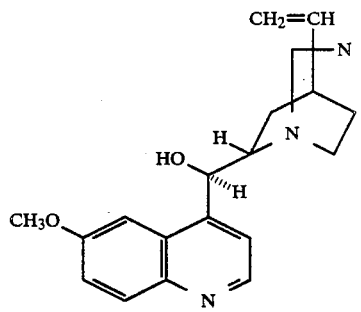

or one or more of its salts.

The citronellyl nitrile/citronellol-containing composition of our invention may be prepared by first reacting citronellal which is a mixture of compounds having the structures:

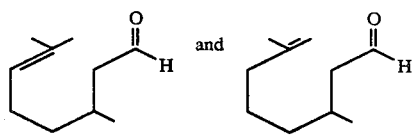

wherein the compound having the structure:

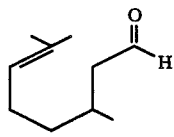

is present in an amount of from about 60% to about 100% with a hydroxylamine acid salt in the presence of base to form an oxime; a mixture of citronellal oximes having the structures:

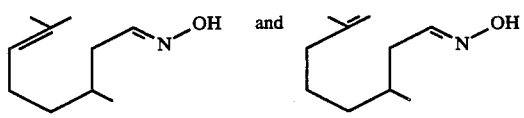

wherein the compound having the structure:

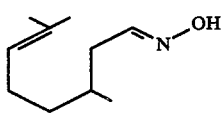

is present in an amount of from about 60% up to about 100%; and then heating the resulting oxime mixture for the resulting oxime to form the nitrile or mixture of nitriles having the structure(s):

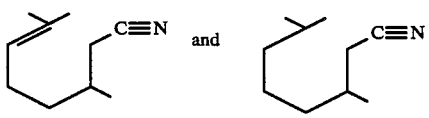

wherein the compound having the structure:

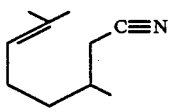

is present in an amount of from about 60% up to about 100%. The reaction for the foregoing process is as follows:

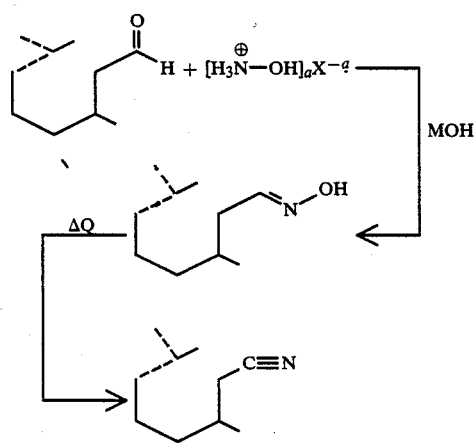

wherein X represents chlorine, bromine or sulfate and "a" represents an integer of from 1 up to 2; wherein in each of the compounds depicted one of the dashed lines represents a carbon-carbon double bond and the other of the dashed lines represents a carbon-carbon single bond; and wherein M represents alkali metal. Biproducts of this process include but are not limited to:

(i) Isopulegol having the structure:

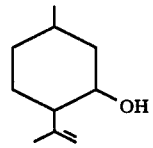

(ii) Citronellol having the structure:

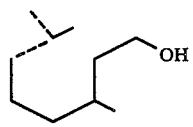

wherein one of the dashed lines represents a carbon-carbon double bond and the other of the dashed lines represents a carbon-carbon single bond (iii) Isopulegyl acetate having the structure:

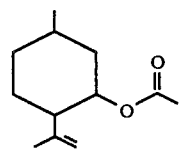

(iv) Caryophyllene having the structure:

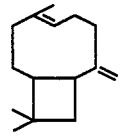

as well as alpha-pinene, beta-pinene, 1,8-Cineole, Limonene, 1,8-Menthadiene, 1,7-Menthadiene, Linalool, p-Menthane-3,8-diol and Citronellal-p-methane-3-8-diol acetal.

The resulting reaction product may be then "worked up" as by saponification and, if desired, subsequent fractional distillation.

Other materials may then be added to the resulting product including the alpha-terpinyl methyl ether, lemon essential oil, and quinine and/or one or more of its salts in the proportion ranges as set forth, supra.

The alpha-terpinyl methyl ether useful in the conjunction with the practice of our invention, may be produced according to the method of Royals, J.Am.-Chem.Soc., 71, 2568-71, (1949) the disclosure of which is incorporated by reference herein. Such disclosure is also set forth together with spectra in Example X at lines 37-60, column 26 of U.S. Pat. No. 4,173,543 issued on Nov. 6, 1979, the specification for which is incorporated by reference herein.

It will be understood herein that the citronellyl nitrile-containing composition of our invention which may include alpha-terpinyl methyl ether as well as the lemon essential oil and the quinine (or one or more of its salts) can be used either pure or in commercially available form. They can also be used in admixture with an acceptable solvent, e.g., food grade ethyl alcohol.

Other carriers for the use of this invention can be selected from a wide group of liquid and solid materials suitable for applying the citronellyl nitrile/citronellol-containing composition of matter of this invention to an area or to an article of manufacture, e.g., a garbage bag. The citronellyl nitrile/citronellol-containing composition of our invention can be conveniently applied, for example, to an article (e.g., in the interstices of polymeric garbage bags), to an area in the form of solutions or emulsions, or adsorbed or absorbed on solid materials, desirably finely divided solid materials such as dust, powders and the like, for example, attapulgite clay, bentonite clay, fuller's earth, diatomaceous earth, vermiculite, ground corn cob and kaolin.

In addition to ethyl alcohol, for liquid compositions, a wide variety of solvents can be used with the citronellyl nitrile/citronellol-containing composition of our invention. For example, solvents such as hexane, kerosene, petroleum distillates and the like (including aromatic hydrocarbons and other aromatic petroleum-based materials) and oxygenated hydrocarbons, desirably alcohols (including the ethanol cited, supra) and ketones such as methanol, ethanol, isopropanol, acetone, methyl isobutyl ketone, methyl ethyl ketone, and the like are satisfactory solvents. It is preferred that the solvent be essentially odorless or have a mild, pleasant odor. Generally, the amount of citronellyl nitrile/citronellol-containing composition of our invention in the carrier ranges from about 0.25% up to about 10% by weight and preferably from about 0.5% up to about 5%.

Liquids in which the citronellyl nitrile/citronellol-containing composition of our invention are insoluble or only sparingly soluble can also be used in the preparation of compositions of this invention. Such liquids will also be referred to from time to time herein as "non-solvents". In such case the composition is in the form of an emulsion or dispersion of the citronellyl nitrile/citronellol-containing composition of our invention in the non-solvent. Water is a preferred liquid because it is odorless, non-toxic and readily compatible with the citronellyl nitrile/citronellol-containing composition of our invention and the surfaces to which such citronellyl nitrile/citronellol-containing composition of our invention are generally applied.

Such non-solvent containing or aqueous compositions can contain surface active agents such as emulsifiers to disperse or emulsify the citronellyl nitrile/citronellol-containing composition of our invention in the water or other liquid in which the citronellyl nitrile/citronellol-containing composition of our invention is insoluble or in which the citronellyl nitrile/citronellol-containing composition of our invention has only limited solubility. Examples of such surface active agents are alkylarylpolyether alcohols, sodium polyglycolether sulfonates, purified sodium lignosulfonate, sodium lauryl alcohol sulfate and the like.

Within the contemplation of our invention the concentrates suited for dispersion in water to prepare sprayable emulsions. Such concentrates contain a relatively large quantity of the citronellyl nitrile/citronellol-containing composition of our invention, a small quantity of an emulsifier sufficient to disperse the material in the non-solvent and an organic solvent of the class described above for the citronellyl nitrile/citronellol-containing composition of our invention. Such concentrates desirably contain from about 20% up to about 60% of the citronellyl nitrile/citronellol-containing composition of our invention and from about 2% up to about 10% of the surface active agent, the remainder being the organic solvent. Such concentrates are conveniently diluted with from about 4 up to about 99 parts of water for each part of concentrate.

In certain preferred embodiments of this invention it has been found that the citronellyl nitrile/citronellol-containing composition of our invention are especially adapted for application from aerosol type spray cans in conjunction with a self-propellant composition. Such self-propellant compositions are especially effective in dispersing the citronellyl nitrile/citronellol-containing composition of our invention in the desired area or on or in the desired article (e.g., garbage bag) and in controlling animals by repelling them from such sprayed area or sprayed article of manufacture. While it is possible to use liquids such as water in conjunction with the surface active agent for the self-propellant compositions, it is preferred that the self-propellant aerosol composition of this invention comprise the citronellyl nitrile/citronellol-containing composition of our invention, a propellant agent and usually a solvent carrier for the citronellyl nitrile/citronellol-containing composition of our invention. The solvents used for the citronellyl nitrile/citronellol-containing composition of our invention are as set forth, supra. The propellant can be any of the aerosol types including lower hydrocarbons such as propane and isobutane, gaseous materials such as carbon dioxide, and the like, or the halogenated hydrocarbons such as dichlorodifluoromethane, dichlorotetrafluoroethane, chlorotrifluoromethane, dichlorofluoromethane and the like. It is preferred in practicing our invention to utilize lower hydrocarbon and carbon dioxide as propellant agents.

It will be understood that where the propellant agent is a solvent for the citronellyl nitrile/citronellol-containing composition of our invention, it can act in this dual capacity and no further solvent will be necessary. The self-propellant compositions of this invention will generally contain from about 0.5 up to about 25% of the citronellyl nitrile/citronellol-containing composition of our invention and from about 2 up to about 50% of the propellant agent, the remainder being solvent or non-solvent plus emulsifier. Generally, it is preferred that the amount of citronellyl nitrile/citronellol-containing composition of our invention be in the range of from about 1 up to about 10% of the self-propellant composition, since lower concentrations citronellyl nitrile/citronellol-containing composition of our invention require that the area be very heavily sprayed to obtain the desired repellant activity. On the other hand, if the composition is too concentrated with respect to the citronellyl nitrile/citronellol-containing composition of our invention, the spray will be difficult to control and will result in wasteful over-application of citronellyl nitrile/citronellol-containing composition of our invention to the area.

It will be understood that the carriers for use herein can also comprise amounts of other adjuvant materials and inert ingredients. For example, the compositions of our invention can also contain other volatile odorants (including perfumes), coloring agents such as dyes and pigments and the like. It is also possible to admix the active ingredients for other purposes with the carrier including, for example, miticides such as methoxychlor, insecticides such as DDT, DDE, dieldrin and malathion, other animal repellants, and insect repellants. For example, a composition can be specially prepared for use on bushes which contains insecticidal or other agents so that the bushes can be made repellant to domestic animals (e.g., dogs) and treated for other conditions at the same time. Thus, an evergreen bush or shrub could be sprayed with the composition of our invention wherein the carrier contains an insecticide and/or insect repellant so that the composition would repel dogs and protect the plant against red spider mites at the same time. Further, if desired, all or part of the citronellyl nitrile/citronellol-containing composition of our invention can be encapsulated by well known techniques to provide for controlled release over a relatively long period of time such as, for example, using the techniques set forth in U.S. Pat. No. 3,971,852 issued on July 27, 1976 (Brenner, et al.) entitled "Process of Encapsulating An Oil and Produced Thereby", the specification for which is incorporated by reference herein.

The following examples are given to illustrate preferred embodiments of this invention as it is now preferred to practice it. It will be understood that these examples are illustrative and the invention is not to be considered as restricted thereto except as indicated in the appended claims.

In all examples set forth, infra, the test methods used are taken from "Test Methods For Vertebrate Pest Control And Management Materials", a symposium sponsored by ASTM, Committee E-35 on Pesticides (*AMERICAN SOCIETY FOR TESTING AND MATERIALS, Monterey, Calif., Mar.* 8, 1976 (ASTM Special Technical Publication 625 by W. B. Jackson and R. E. March)) [American Society For Testing and Materials, 1916 Race Street, Philadelphia, Pa. 19103]; article published therein at page 123 by C. C. Snider and J. A. McCann entitled "Proposed Efficacy Test for Aerosol Dog Repellents that Are Designed to Reduce Damage to Garbage Bags".

More specifically, in each of the examples set forth, infra, the Snider and McCann Efficacy Test was designed to provide data to support a claim that the given material can reduce damage to garbage bags to a greater extent than a second given material.

A minimum of eight dogs are tested individually within rectangular arenas for one hour on each of four days. Three garbage bags are placed at each end of each arena. The bags at one end of the arenas are treated with the repellent to be tested (in this case mixtures of citronellyl nitrile/citronellol-containing composition of our invention (referred to as "treated bags A")) and those at the other end are treated with a known prior art commercially available repellent, e.g., methyl nonyl ketone (referred to as "treated bags B"). The bags are appropriately sprayed and stored for the maximum length of time (prior to testing) for which efficacy is desired to be claimed. The amount of ration placed in each bag is calculated to give the dog one third of an "adequate" amount of nutrients. Consequently, the dog receives free choice between "treated bags A" and "treated bags B" and is not forced by hunger to open any of the "treated bags A". The damage to a bag is recorded as "opened" or "unopened". Dogs are divided into groups of four and a four by four Graeco-Latin square containing days, arenas, dogs and point of introduction into the arenas is constructed for each group. Percent repellency is calculated for each day, each dog, and the total test. Reference tests using six untreated bags are employed as checks on the activity of the dogs in repellent tests.

The Snider and McCann article entitled "Proposed Efficacy Test for Aerosol Dog Repellents that Are Designed to Reduce Damage to Garbage Bags" is incorporated by reference herein.

In the instant specification and throughout the following examples the term "lemon essential oil" is intended to mean "oil of lemon" having an origin in citrus limon and termed "oleum limonis" as defined on pages 81-115, inclusive, of "The Essential Oils" by Ernest Guenther, Vol. 3, published by Robert E. Krieger Publishing Co., Box 542, Huntington, N.Y. 11743 (reprint, 1974); original edition 1949, published by Van Nostrand Reinhold Co., 1949, including, but not limited to:

(i) California Lemon Oil;
(ii) Italian Lemon Oil;
(iii) Terpeneless Italian Lemon Oil;
(iv) Sesquiterpeneless Italian Lemon Oil;
(v) Brazilian Lemon Oil; and
(vi) Israel Lemon Oil, each of which contains materials selected from the group consisting of (i) Alpha-Pinene;
(ii) Camphene;
(iii) β-Pinene
(iv) Phellandrene;
(v) Methyl heptenone;
(vi) Gamma-Terpinene;
(vii) d-Limonene;
(viii) Octaldehyde;
(ix) Citronellol;
(x) Alpha-Terpineol;
(xi) Citral;
(xii) Linalyl acetate;
(xiii) Geraniol;
(xiv) Geranyl acetate;
(xv) Nerol;
(xvi) Neryl acetate;
(xvii) Citronellyl acetate;
(xviii) Bisabolene;
(xix) Cadinene;
(xx) Acetic acid;
(xxi) Capric acid;
(xxii) Lauric acid;
(xxiii) Methyl anthranilate;
(xxiv) Limettin; and
(xxv) Linalool.

The Italian Lemon Oils include but are not limited to:
Sfumatrici (Andnonaco);
Sfumatrici (Morasco);
Sfumatrici (Cannayo);
Peratoner (Process:Distilled);
Rotary Rasping (Centrifuged);
Cannavo (Whole Fruit);
Speciale (Whole Fruit);
Special (Bennett-Cusmano Process);
Avena (Whole Fruit);
Avena (Bennett-Cusmano Process); and
Sponge.

The disclosure of the Guenther reference cited, supra, is incorporated herein by reference.

DETAILED DESCRIPTION OF THE DRAWINGS

FIG. 1 is a schematic cutaway elevation diagram of the extrusion pelletizing apparatus useful in carrying out a process whereby the animal repellent composition of our invention, the composition comprising citronellyl nitrile/citronellol-containing composition of our invention is incorporated into a polymer for a subsequent formation of functional articles containing such a composition. Motor 15 drives the extruder screws located at 23A and barrel 16, the extruder being operated at temperatures in the range of from about 150° C. up to about 250° C. At the beginning of the barrel, resin at source 12 together with additives, e.g., opacifiers, processing aids, colors, pearlescent agents and densifiers at location 13 is added via addition funnel 14 into the extruder. Simultaneously (when the operation reaches "steady state") the animal repellent material which comprises citronellyl nitrile/citronellol-containing composition of our invention is added to the extruder at one, two or more of barrel segments 3–8 (shown as S3, S4, S5, S6, S7 and S8) of the extruder (which may be a twin screw or single screw extruder) at locations 18a, 18b, 18c and 18d by means of gear pump 23 from source 17. From source 19 into barrel segments 5–10 (shown as S3, S4, S5, S6, S7 and S8), optionally, a gaseous or liquid blowing agent, e.g., nitrogen, carbon dioxide and the like, are added simultaneously with the addition of the animal repellent material. The feed range of resin is about 80–300 lbs. per hour. The feed rate range of the animal repellent composition comprising the citronellyl nitrile/citronellol-containing composition of our invention is between 1 and 35% of the feed rate range or the resin. The blowing agent rate range is such that the pressure of the gas or the pressure over the liquid being fed into the extruder is between about 50 and 200 psig. If desired, the extruded ribbon or cylinder may be passed through water bath 20 and pelletizer 21 into collection apparatus 21a. A detailed description of the operation of this apparatus is disclosed in U.S. Pat. No. 4,521,541 issued on June 4, 1985, the specification for which is incorporated by reference herein.

Figure 2:
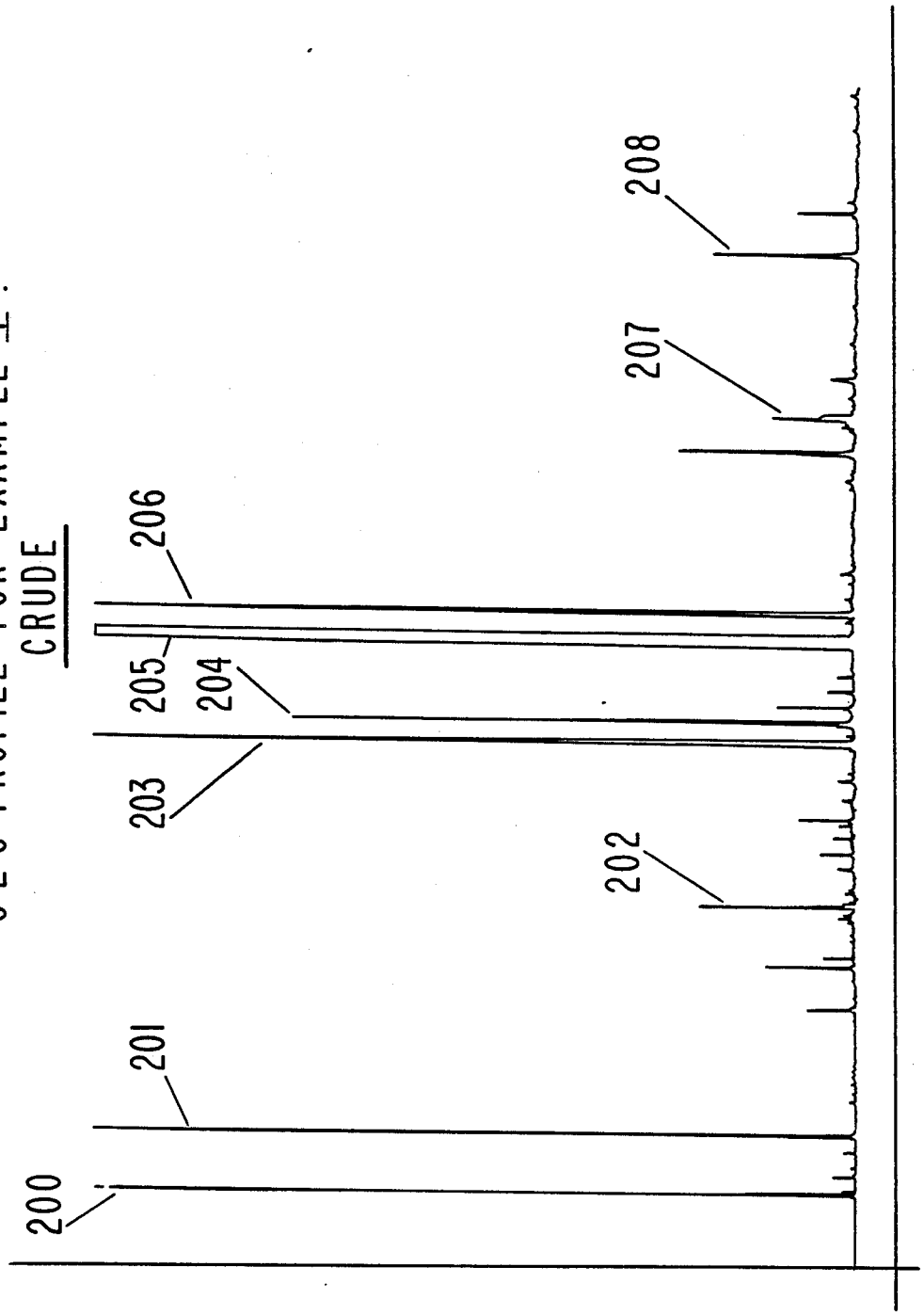
FIG. 2 is the GLC profile for the crude reaction product of Example I containing citronellyl nitrile, citronellol, citronellal oxime, isopulegyl, 1,8-cineole, limonene and beta caryophyllene as well as other reaction biproducts (Conditions: 50 m×0.32 mm fused silica/methyl silicone column programmed at 75°–225° C. at 2° C. per minute).

FIG. 2 is the GLC profile for the crude reaction product of Example I set forth, infra wherein citronellyl nitrile and citronellol are produced. FIG. 2 is a "fused silica capillary survey" (Conditions: 50 m×0.32 mm fused silica/methyl silicone column programmed at 75°–225° C. at 2.0° C. per minute).

The peak indicated by reference numeral 200 is the peak for methanol (solvent). The peak indicated by reference numeral 201 is the peak for the toluene solvent. The peak indicated by reference numeral 202 is the peak for the mixture of 1,8-cineole and limonene. The peak indicated by reference numeral 203 is the peak for isopulegyl. The peak indicated by reference numeral 204 is also a peak for isopulegyl. The peak indicated by reference numeral 205 is the peak for citronellyl nitrile. The peak indicated by reference numeral 206 is the peak for citronellol. The peak indicated by reference numeral 207 is the peak for the mixture of p-menthane-3,8-diol and citronellal oxime. The peak indicated by reference numeral 208 is the peak for beta-caryophyllene.

Figure 3:
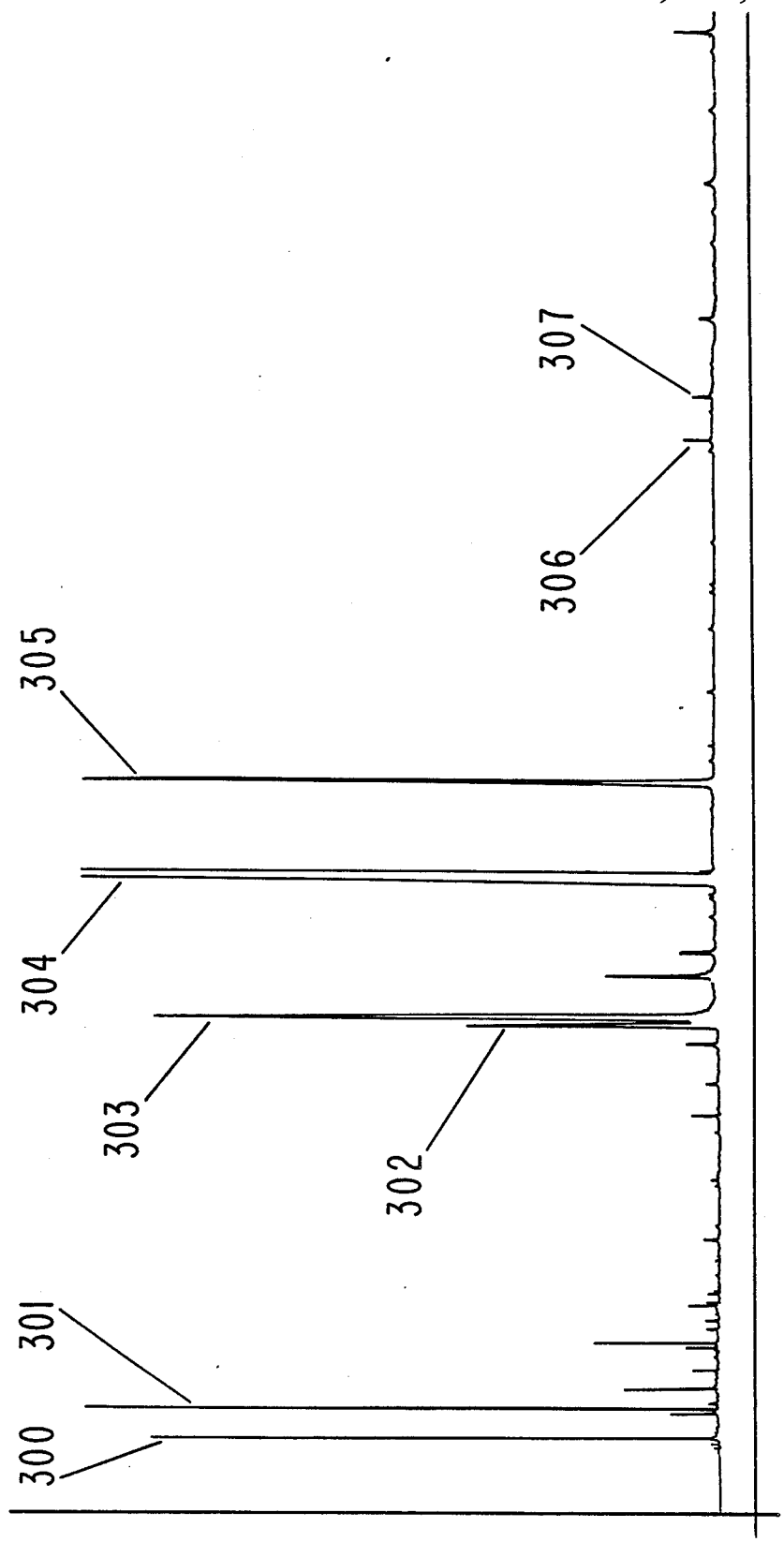
FIG. 3 is the GLC profile of the crude reaction product of Example I after saponification said crude reaction product containing isopulegyl, citronellyl nitrile, citronellol, citronellyl oxime, beta caryophyllene and other reaction side products (Conditions: 50 m×0.32 mm fused silica/carbowax 20 M column programmed at 75°–225° C. at 2° C. per minute).

FIG. 3 is the GLC profile for the crude reaction product of Example I after saponification (see Example I, infra). (Conditions: 50 m×0.32 mm fused silica/carboxwax 20 M column programmed at 75°–225° C. at 2.0° C. per minute).

The peak indicated by reference numeral 300 is the peak for the methanol solvent. The peak indicated by reference numeral 301 is the peak for the toluene solvent. The peak indicated by reference numeral 302 is the peak for isopulegyl. The peak indicated by reference numeral 303 is also a peak for isopulegyl. The peak indicated by reference numeral 304 is a peak for citronellyl nitrile. The peak indicated by reference numeral 305 is a peak for citronellol. The peak indicated by reference numeral 306 is the peak for citronellal oxime. The peak indicated by reference numeral 307 is also a peak for citronellal oxime.

Figure 4:
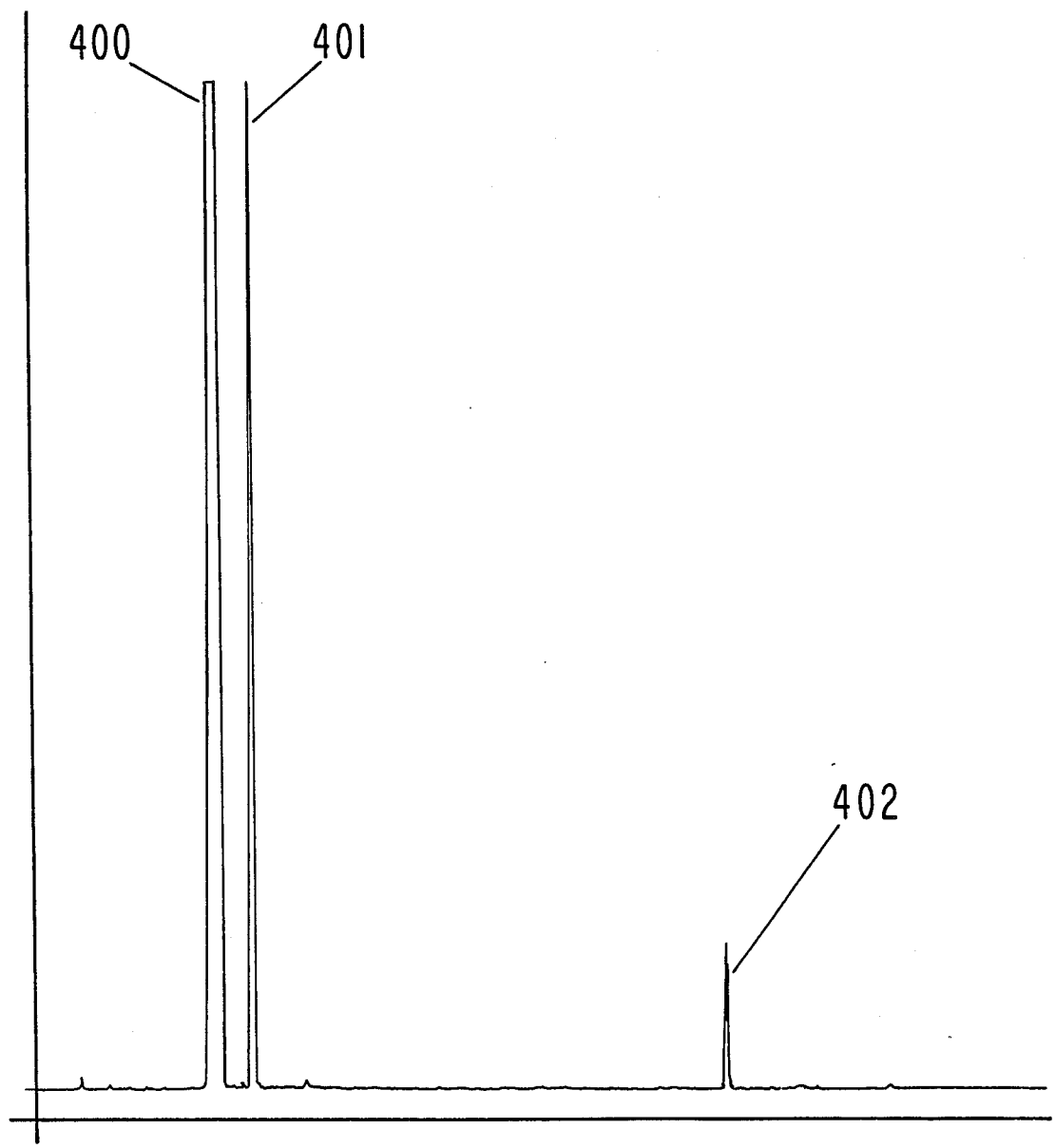
FIG. 4 is the GLC profile (fused silica capillary survey) of the reaction product of Example I containing citronellyl nitrile, citronellol, beta caryophyllene and isopulegol (Conditions: 50 m×0.32 mm fused silica/methyl silicone column programmed at 75°–225° C. at 2.0° C. per minute).

FIG. 4 is the GLC profile for the fused silica capillary survey of the reaction product of Example I. The peak indicated by reference numeral 400 is the peak for citronellyl nitrile. The peak indicated by reference numeral 401 is the peak for citronellol. The peak indicated by reference numeral 402 is the peak for beta caryophyllene. (Conditions: 50 m×0.32 mm fused silica/methyl silicone column programmed at 75°–225 C. at 2.0° C. per minute).

Figure 5:
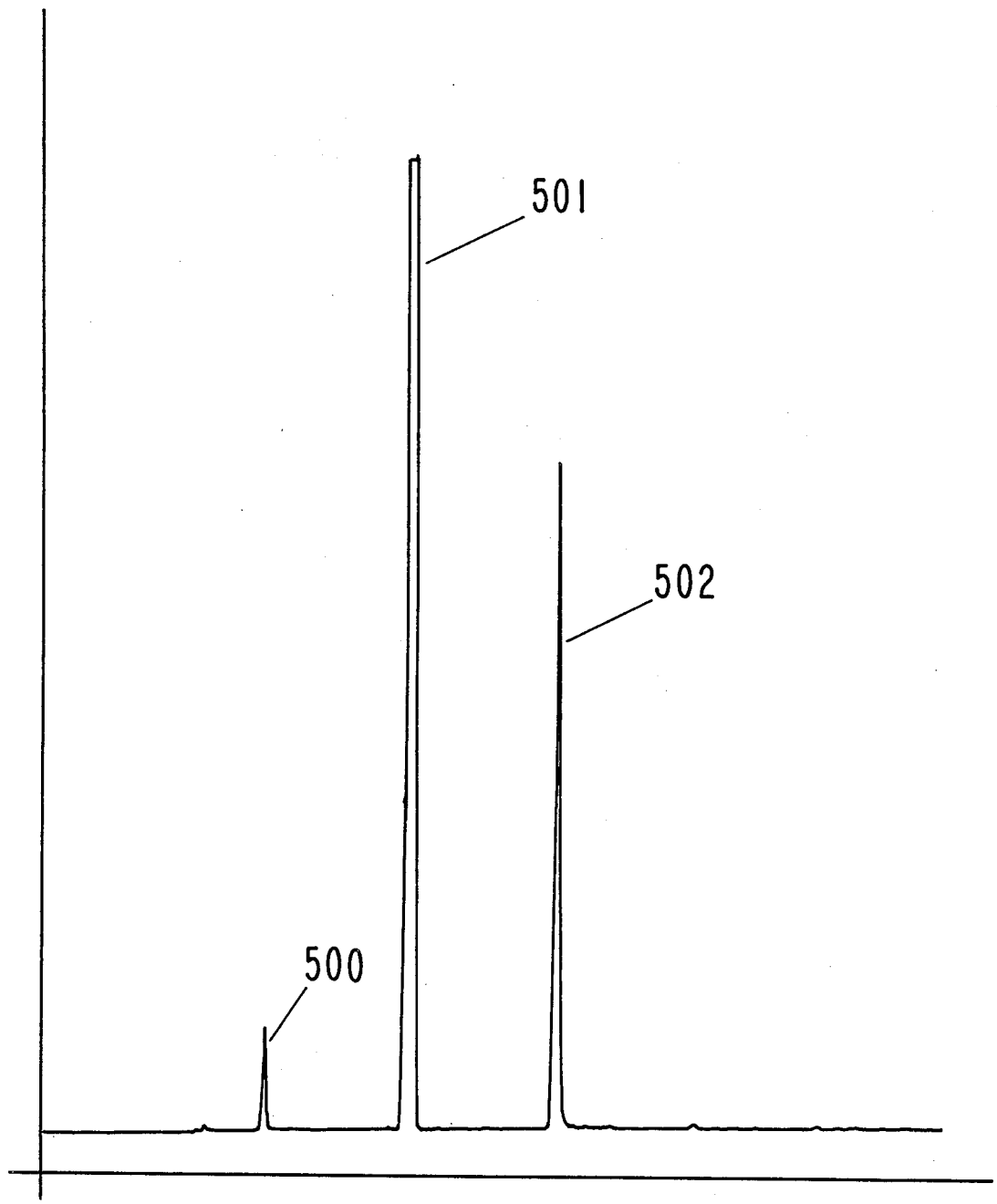
FIG. 5 is the fused silica capillary survey of the reaction product of Example I containing beta caryophyllene, citronellyl nitrile and citronellol (Conditions: 50 m×0.32 mm fused silica/carbowax 20 M column programmed at 75°–225° C. at 2.0° C. per minute).

FIG. 5 is the GLC profile for the fused silica capillary survey of the reaction product of Example I using a carbowax 20 M column (Conditions: 50 m×0.32 mm fused silica/carbowax 20 M column programmed at 75°–225°C. at 2.0° C. per minute). The peak indicated by reference numeral 500 is the peak for beta caryophyllene. The peak indicated by reference numeral 501 is the peak for citronellyl nitrile. The peak indicated by reference numeral 502 is the peak for citronellol.

The following examples set forth preferred ways to practice our invention. These examples are not to be construed as limiting our invention. Our invention is only to be limited by the claims appended hereto.

EXAMPLE I

PREPARATION OF CITRONELLYL NITRILE/CITRONELLOL-CONTAINING COMPOSITION

Reaction:

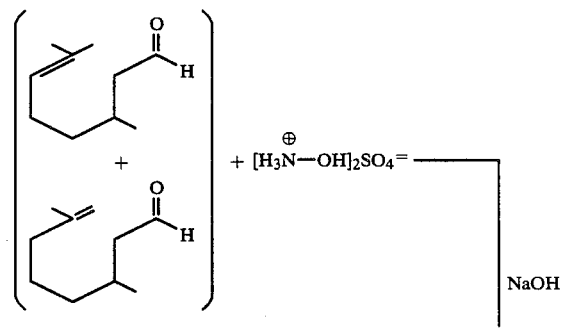

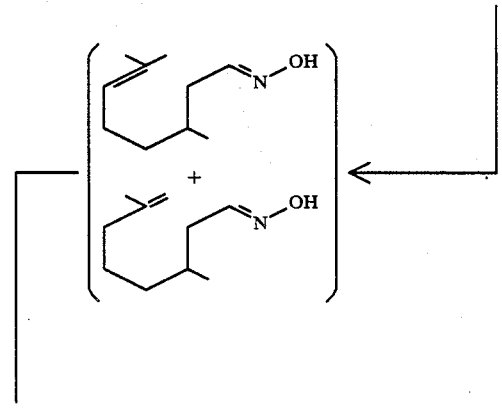

Reaction:

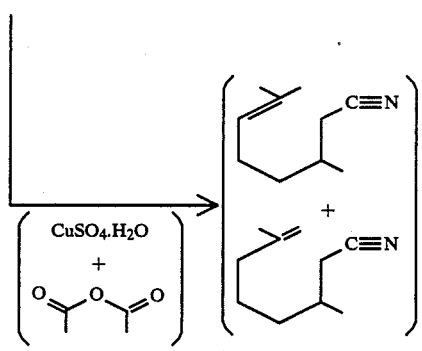

Into a 3000 gallon stainless steel reactor equipped with steam heat and water cooling in the jacket and ethylene glycol cooling in cooling coils is placed 2200 pounds of hydroxyl amine sulfate and 200 gallons of water, with stirring while maintaining the temperature at 20°–30° C. After the solids are dissolved the hydroxyl amine sulfate solution is cooled to 0°–5° C.

5100 Pounds of citronellal is then added to the reaction mass with stirring under a nitrogen blanket while maintaining the temperature at 0°–5° C.

Also while maintaining the temperature at 0°–5° C., 11,000 pounds of a 50% solution of sodium hydroxide is pumped into the reaction mass at such a rate that the temperature remains in the range of 0°–5° C.

The rate of addition of the 50% solution of sodium hydroxide is approximately 10 pounds per minute.

The reaction mass is then stirred for a period of two hours at 0°–5° C.

The reaction mass is then extracted with 3000 pounds of toluene by first admixing the toluene with the reaction mass and then heating the reaction mass up to 25° C. and agitating for 0.5 hours. The aqueous layer is removed and discarded and the toluene extract is then washed with 300 pounds of a saturated sodium chloride solution at 30° C.

The organic phase contains 35% toluene and 50% citronellal oxime.

The organic phase is then metered at the rate of 20 pounds per minute into the stainless steel reaction vessel in which has been placed 4500 pounds of acetic anhydride and 24 pounds of copper sulfate monohydrate while refluxing the reaction mass at 85°–90° C. The reaction mass is then stirred at reflux for a period of one hour.

The reaction mass is then cooled to 30° C. and 5000 gallons of water are added to the reaction mass with stirring.

At this point in time the reaction mass contains
 about 40% citronellyl nitrile;
 about 30% toluene;
 about 5% isopulegyl acetate; and
 about 8% citronellyl acetate.

The GLC profile for the crude product is set forth in FIG. 2 and described in detail, supra.

The reaction mass is then admixed with 50% sodium hydroxide (1000 gallons) in order to saponify the citronellyl acetate and isopulegyl acetate. After adding the 50% sodium hydroxide to the reaction mass, the reaction mass is admixed with 1500 pounds of methanol and the resulting mixture is refluxed for a period of one hour at 80° C. As a result of the saponification, the isopulegyl acetate and citronellyl acetate are reduced to below 0.5% each and replaced by isopulegyl and citronellol.

The reaction mass is then admixed at the rate of 0.1% with Ionol ® and 4% by weight of Primol ® after washing with 2000 gallons of water.

The saponified reaction product has a GLC profile as set forth in FIG. 3 described in detail, supra.

The resulting saponified product is then fractionally distilled first at 100 mm/Hg. pressure at a head temperature of 55° C. and a pot temperature of 120° C.; and at a pressure of 3 mm/Hg. and a head temperature in the range of 77°–78° C. and a pot temperature in the range of 103°–106° C. (reflux ratio 9:1). The resulting product contains:
 85.51% citronellyl nitrile;
 12.80% citronellol;
 1.36% beta caryophyllene;
 0.1% isopulegyl.

FIGS. 4 and 5 are the GLC profiles for the distillation product and these GLC profiles are described in detail, supra.

EXAMPLE II

Using the apparatus of FIG. 1, at the rate of 1%, the citronellyl nitrile/citronellol-containing mixture produced according to Example I is placed in polyethylene and a blown film is produced and formed into garbage bags. The technique used is that set forth in U.S. Pat. No. 4,521,541 issued on June 4, 1985 incorporated herein by reference.

The garbage bags are compared with garbage bags containing methyl nonyl ketone also at the rate of 1% in the garbage bags and the results are as follows:

| RUN 1 | Bags Opened By Dogs | Bags Remaining Closed | Total |
|---|---|---|---|
| Citronellyl Nitrile Mixture | 6 | 18 | 24 |
| Methyl Nonyl Ketone | 15 | 9 | 24 |
| TOTAL: | 21 | 27 | 48 |

Degrees of Freedom = 1
Calculated CHI Square = 6.8
AT DF = 1, CHI Square at Alpha = 0.05 = 3.841
CHI Square at Alpha = 0.10 = 2.706

| RUN 2 | Bags Opened By Dogs | Bags Remaining Closed | Total |
|---|---|---|---|
| Citronellyl Nitrile Mixture | 8 | 16 | 24 |
| Methyl Nonyl Ketone | 14 | 10 | 24 |
| TOTAL: | 22 | 26 | 48 |

Degrees of Freedom = 1
Calculated CHI Square = 3.01
AT DF = 1, CHI Square at Alpha = 0.05 = 3.841
CHI Square at Alpha = 0.10 = 2.706

| COMBINED RUNS 1 AND 2 | | | |
|---|---|---|---|
| | Bags Opened By Dogs | Bags Remaining Closed | Total |
| Citronellyl Nitrile Mixture | 14 | 34 | 48 |

-continued

| | COMBINED RUNS 1 AND 2 | | |
|---|---|---|---|
| | Bags Opened By Dogs | Bags Remaining Closed | Total |
| Methyl Nonyl Ketone | 29 | 19 | 48 |
| TOTAL: | 43 | 53 | 96 |

| | |
|---|---|
| Degrees of Freedom | = 1 |
| Calculated CHI Square | = 9.47 |
| AT DF = 1, CHI Square at Alpha = 0.05 is | = 3.841 |
| CHI Square at Alpha = 0.10 is | = 2.706 |
| CHI Square at Alpha = 0.01 is | = 6.635 |

The results of the foregoing experiments prove that the citronellyl nitrile/citronellol-containing mixtures of our invention have unexpected, unobvious and advantageous properties as an animal repellent.

What is claimed is:

1. A method for repelling dogs which consists of applying to an area or article of manufacture a dog repellent amount of a composition of matter contained in a solid or liquid carrier, said composition of matter consisting essentially of:

(a) from about 40 parts by weight up to about 90 parts by weight of citronellyl nitrile which is a mixture containing from about 60 up to about 100% by weight of the compound having the structure:

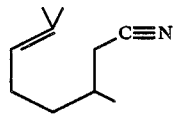

and from about 0 up to about 40% by weight of the compound having the structure:

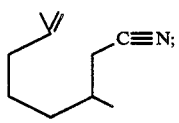

(b) from about 4 parts by weight up to about 20 parts by weight of citronellol which is a mixture of compounds containing from about 60% up to about 100% by weight of the compound having the structure:

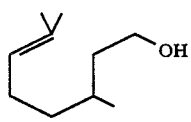

and from about 0 up to about 40% by weight of the compound having the structure:

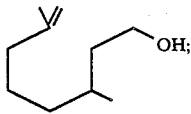

(c) from about 0 up to about 2 parts by weight of beta-caryophyllene having the structure:

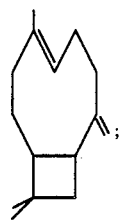

(d) from about 0 up to about 0.5 parts by weight of isopulegyl acetate having the structure:

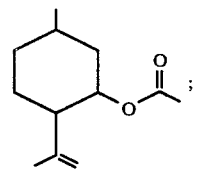

(e) from about 0 up to about 1.5 parts by weight of the isopulegol having the structure:

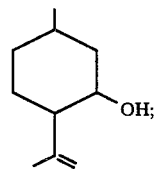

(f) from about 0 parts by weight up to about 50 parts by weight of alpha-terpenyl methyl ether having the structure:

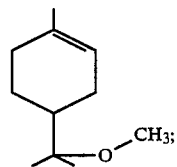

(g) from about 0 parts by weight up to about 50 parts by weight of lemon essential oil;

(h) from about 0 parts by weight up to about 25 parts by weight of quinine having the structure:

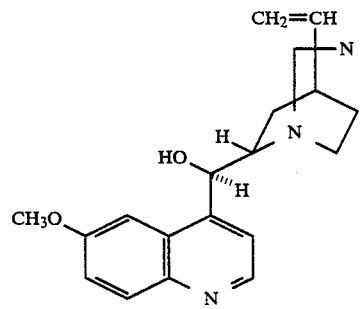

or one or more of its salts.

2. The method for repelling dogs of claim 1 wherein the carrier of said dog repellent amount of said composition of matter is a liquid and is a solvent for said composition of matter.

3. A method of repelling dogs of claim 1 wherein said composition of matter consists essentially of:
   82–90% citronellyl nitrile;
   9–17% citronellol;
   0–2% beta-caryophyllene;
   0–0.5% isopulegyl acetate; and
   0–1.2% isopulegol.

4. The method of claim 3 wherein the carrier for the dog repellent amount of said composition of matter is a liquid and is a solvent for said composition of matter.

5. A method of manufacturing a polymeric article which will repel dogs comprising using in the manufacture of the article a polymer which has been admixed with a dog repelling amount of a composition of matter consisting essentially of:
   (a) from about 40 parts by weight up to about 90 parts by weight of citronellyl nitrile which is a mixture containing from about 60 up to about 100% by weight of the compound having the structure:

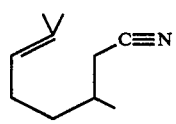

and from about 0 up to about 40% by weight of the compound having the structure:

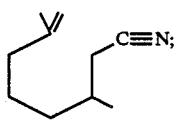

(b) from about 4 parts by weight up to about 20 parts by weight of citronellol which is a mixture of compounds containing from about 60% up to about 100% by weight of the compound having the structure:

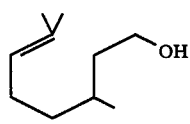

and from about 0 up to about 40% by weight of the compound having the structure:

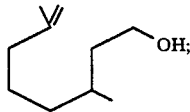

(c) from about 0 up to about 2 parts by weight of beta-caryophyllene having the structure:

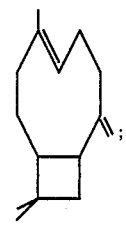

(d) from about 0 up to about 0.5 parts by weight of isopulegyl acetate having the structure:

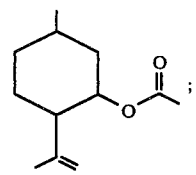

(e) from about 0 up to about 1.5 parts by weight of the isopulegol having the structure:

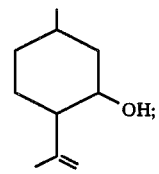

(f) from about 0 parts by weight up to about 50 parts by weight of alpha-terpenyl methyl ether having the structure:

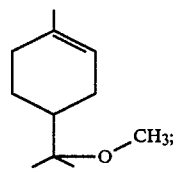

(g) from about 0 parts by weight up to about 50 parts by weight of lemon essential oil;
   (h) from about 0 parts by weight up to about 25 parts by weight of quinine having the structure:

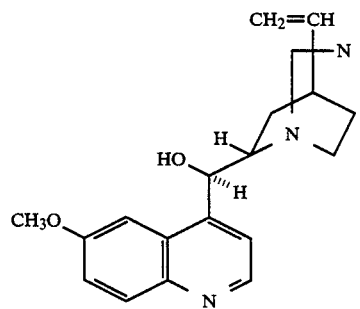

or one or more of its salts.

6. A method for repelling dogs which comprises applying to an area or article of manufacture a dog repelling amount of a composition of matter consisting of:

(a) from about 40 parts by weight up to about 90 parts by weight of citronellyl nitrile which is a mixture containing from about 60 up to about 100% by weight of the compound having the structure:

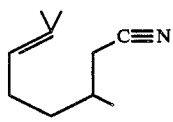

and from about 0 up to about 40% by weight of the compound having the structure:

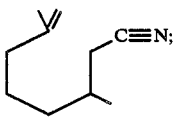

(b) from about 4 parts by weight up to about 20 parts by weight of citronellol which is a mixture of compounds containing from about 60% up to about 100% by weight of the compound having the structure:

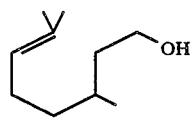

and from about 0 up to about 40% by weight of the compound having the structure:

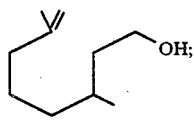

(c) from about 0 up to about 2 parts by weight of beta-caryophyllene having the structure:

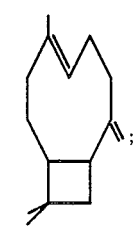

(d) from about 0 up to about 0.5 parts by weight of isopulegyl acetate having the structure:

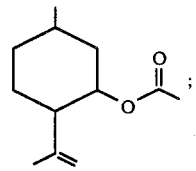

(e) from about 0 up to about 1.5 parts by weight of the isopulegol having the structure:

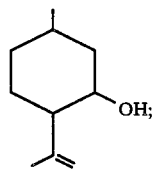

(f) from about 0 parts by weight up to about 50 parts by weight of alpha-terpenyl methyl ether having the structure:

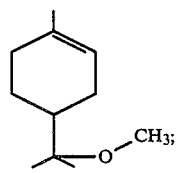

(g) from about 0 parts by weight up to about 50 parts by weight of lemon essential oil;
(h) from about 0 parts by weight up to about 25 parts by weight of quinine having the structure:

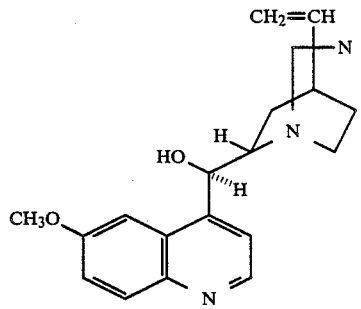

or one or more of its salts, said composition of matter being adsorbed on a solid selected from the group consisting of attapulgite clay, bentonite clay, fuller's earth, diatomaceous earth, vermiculite, ground corn cob and kaolin.

* * * * *